United States Patent [19]
Petöcz et al.

[11] Patent Number: 4,873,249
[45] Date of Patent: Oct. 10, 1989

[54] PHARMACEUTICAL COMPOSITION

[75] Inventors: Lujza Petöcz; István Simonyi; Iván Beck; Gábor Gigler; Márton Fekete; Enikö Kiszelly; Attila Mándi; Frigyes Görgényi; András Dietz; Katalin Sümeg née Zukovics; Elemér Jákfalvi, all of Budapest, Hungary

[73] Assignee: EGIS Gyogyszergyar, Budapest, Hungary

[21] Appl. No.: 17,090

[22] Filed: Feb. 20, 1987

[30] Foreign Application Priority Data

Feb. 28, 1986 [HU] Hungary .................................. 842/86

[51] Int. Cl.$^4$ ............................................ A61K 31/505
[52] U.S. Cl. ...................................... 514/275; 514/825
[58] Field of Search ............... 514/275, 258, 352, 825

[56] References Cited

U.S. PATENT DOCUMENTS

| 4,053,608 | 10/1977 | Morisawa et al. | 514/352 |
|---|---|---|---|
| 4,332,796 | 6/1982 | Los | 514/157 |
| 4,461,765 | 7/1984 | Takagishi et al. | 514/158 |

OTHER PUBLICATIONS

Francalanci et al., Chem. Abst. 79(25):142830a (1973).

*Primary Examiner*—Douglas W. Robinson
*Assistant Examiner*—R. Kearse
*Attorney, Agent, or Firm*—Keil & Weinkauf

[57] ABSTRACT

The invention relates to pharmaceutical compositions having analgesic and/or anti-inflammatory effect comprising as active ingredient 2,4-diamino-5-(3,4-dimethoxy-benzyl)-pyrimidine or a pharmaceutically acceptable acid addition salt thereof.

The pharmaceutical compositions of the present invention exhibit the desired analgesic and anti-inflammatory effect without causing undesired ulcerogenic side-effects.

7 Claims, No Drawings

PHARMACEUTICAL COMPOSITION

This invention relates to pharmaceutical compositions and a process for the preparation thereof.

According to the present invention there are provided pharmaceutical compositions comprising as active ingredient an effective amount of 2,4-diamino-5-(3,4-dimethoxy-benzyl)-pyrimidine or a pharmaceutically acceptable acid addition salt thereof in admixture with suitable inert solid or liquid pharmaceutical carriers.

According to a particularly preferred embodiment of the present invention there are provided pharmaceutical compositions having analgesic and/or anti-inflammatory effect comprising as active ingredient an effective amount of 2,4-diamino-5-(3,4-dimethoxy-benzyl)-pyrimidine or a pharmaceutically acceptable acid addition salt thereof in admixture with suitable inert solid or liquid pharmaceutical carriers.

It is known that 2,4-diamino-5-(3,4-dimethoxy-benzyl)-pyrimidine can be used in veterinary medicine for the treatment of poultry coccidiosis. It is known further that 2,4-diamino-5-(3,4-dimethoxybenzyl)-pyrimidine is also useful in veterinary medicine in combination with sulfaquinoxaline as anti-protozoic agent (Brit J. Pharmacol. 6, 185–200 /1951/; Antibiotics and Chemotherapy 4, 971–977 /1954/; Antibiotics and Chemotherapy 10, 556–564 /1960/; J. Med. Pharm. Chem 5, 1103–1123 /1962/; Vet. Record. 17, /43/ 1252–1256 /1965/).

Prior art is completely silent in teaching any use of 2,4-diamino-5-(3,4-dimethoxybenzyl)-pyrimidine in human therapy.

It has been found surprisingly that 2,4-diamino-5-(3,4-dimethoxybenzyl)-pyrimidine (referred to further on as Compound A) and its acid-addition salts possess useful and characteristic features in human clinical use. Compound A and its salts show especially outstanding analgesic and anti-inflammatory activities which surpass the effect of the reference compounds used in therapy for this purpose and it surpasses them by several orders of magnitude as far as the therapeutic indices are concerned. A particularly important advantage of Compound A is that it does not induce any harmful side effect in the gastric mucosa, like other well-known analgesic and anti-inflammatory agents. Compound A is very slightly toxic. The slight sedative activity of Compound A in painful illnesses may be taken as a favourable complemantary action. Compound A has an anti-pyretic activity, however does not shown any influence on the normal body temperature. In addition Compound A inhibits the chronic inflammation (adjuvant arthritis).

The analgesic, acute and chronic anti-inflammatory, anti-pyretic and sedative activities of Compound A are proved by the tests below. Furthermore animal experiments prove that Compound A does not induce gastric mucosal damage.

(1) ACUTE TOXICITY IN MICE AND RATS METHOD

The experiments were performed in CFLP white mice of both sexes of 18–22 g body weight and in Wistar rats of both sexes weighing 110–150 g in groups of at least 10 animals. Compound A was applied p.o. dissolved in a solution containing 0.2% Tween-80 in distilled water in a volume of 20–30 ml/kg in mice and 10 ml/kg in rats. The observation period after treatment lasted for 14 days.

Statistical evaluation was carried out as described by Litchfield-Wilcoxon's method.

(2) ANALGESIC ACTIVITY "WRITHING TEST" IN MICE METHOD

Mice weighing 20–25 g were injected intraperitoneally with 0.75% (v/v) acetic-acid in a volume of 20 ml/kg, according to the method of Newbould (1969). Between the 5th and 10th minute after the administration of acetic acid total number of the typical writhing reactions was counted, and expressed as percentage of the control. The experiments were performed in groups of at least 12 mice; measurements were done 60 min. after oral application of the test compounds.

"WRITHING TEST" IN RATS METHOD

Rats weighing 130–170 g were administered intraperitoneally 0.75% (v/v) acetic acid in a volume of 8 ml/kg. Five minutes after treatment with acetic acid, total number of characteristic writhing reactions was counted for 10 minutes and expressed as percentage of the control group. One hour prior to the injection of acetic acid, rats (10 per dose group) were treated with Compound A or vehicle p.o.

TABLE 1

Acut toxicity and analgesic activity in mice

| Test-compound | $LD_{50}$ mg/kg | Writhing test $ID_{50}$ mg/kg | TI |
|---|---|---|---|
| Compound A | 6028.3 | 141.1 | 42.7 |
| Acetylsalicylic acid | 1350.0 | 260.8 | 5.2 |
| Paracetamol | 510.0 | 180.0 | 2.8 |
| Phenylbutazone | 1000.0 | 100–200 | 5–10 |

TI = therapeutic index

TABLE 2

Acut toxicity and analgesic activity in rats

| Test-compound | $LD_{50}$ mg/kg | Writhing test $ID_{50}$ mg/kg | TI |
|---|---|---|---|
| Compound A | 3679.3 | 36.0 | 102.2 |
| Indomethacin | 25.5[x] | 4.7 | 5.4 |
| Phenylbutazone | 400.0 | 19.7 | 20.3 |

[x] = Barron D. J. et. al.: Brit. J. Pharmacol. Chem. 33, 396 (1968)

(3) ANTI-INFLAMMATORY ACTIVITY METHOD

Inhibitory activity in carrageenin-induced oedema test was assessed in rats using the technique of Winter at al. (1962). Carageenin (0.1 ml of 1.0% solution) was injected into the plantar surface of the hind paw of rats weighing 130–160 g. Rats were fasted for 12 hours and received drinking water ad libitum. One hour before treatment with the test compound animals were hydrated orally with 30 ml/kg of tap water. The test compounds or the vehicle were administered p.o. in a volume of 10 ml/kg, then two hours later carrageenin was applied. The paw volume was determined in a plethysmometer prior to and 3 hours after administration of the irritant.

TABLE 3

Inhibition of carrageenin-induced oedema in rats

| Test-compound | Dose mg/kg | % inhibition |
|---|---|---|
| Compound A | 125 | 42.0 |

TABLE 3-continued

Inhibition of carrageenin-induced oedema in rats

| Test-compound | Dose mg/kg | % inhibition |
|---|---|---|
| Phenylbutazone | 25 | 56.6 |
| Indomethacin | 1 | 40.3 |
| Acetylsalicylic acid | 100 | 29.5 |

Compound A is more active than acetylsalicylic acid and less effective than Indomethacin and Phenylbutazone.

(4) MEASUREMENT OF ULCEROGENIC ACTIVITY METHOD

Compound A and Indomethacin were applied orally 6 and 16 hours before decapitation (in groups of 10 rats). The controls received the solvent (solvent of Compound A: Tween-80 0.2% v/v in water; the solvent of Indomethacin: CMC (Carboxy-Methyl-Celulose) 0.5% v/v in water). Damages of gastric mucosa were registered (Table 4).

TABLE 4

| Test-compound | Dose mg/kg | Ulcus-index |
|---|---|---|
| Control | — | 0 |
| Compound A | 250 | 0.5 |
|  | 500 | 0.2 |
|  | 1000 | 0 |
| Indomethacin | 5 | 0.2 |
|  | 10 | 1.2 |
|  | 20 | 3.0 |

Indomethacin increases does dependently the ulcus-index, Compound A induces only small alteration even in high doses, this effect of Compound A is independent of the dose employed.

(5) EFFECT ON GASTRIC SECRETION IN RATS METHOD

The experiments were carried out following the surgical method of Shay et al. (1946). Fasted Wistar rats weighing 200–250 g were used. During a 48 hours, starving period rats received drinking water ad libitum. The experimental groups consisted of 4 males and 4 females.

On the day of experiment the pylorus of rats was ligated under ether anaesthesia. Doses of Compound A were applied orally in a solution containing 0.2% of Tween-80 in distilled water 3 hours before the operation. The control groups were treated simultaneously with identical volumes of vehicle in identical route of administration.

Four hours after operation rats were killed with ether, their stomach was removed after cardia ligature, the stomach contents were separated and after centrifugation the volume of the gastric juice was measured. The free acid and total acid content were assayed by titration with 0.1 N NaOH.

The results were individually transformed for 100 g body weight and statistically evaluated by Wilcoxon's method.

TABLE 5

| Test-Compound | Dose mg/kg | Gastric juice ml | Free acid | Total content, ml |
|---|---|---|---|---|
| Control | — | 2.57 | 2.82 | 3.87 |
| Compound A | 250 | 3.01 | 2.17 | 4.33 |
| Control | — | 2.54 | 2.70 | 3.78 |
| Compound A | 500 | 2.93 | 2.18 | 4.40 |
| Control | — | 2.60 | 2.97 | 3.98 |
| Compound A | 1000 | 2.23 | 1.24 | 3.18 |

TABLE 6

| Test-compound A Dose mg/kg | No. of animals | % inhibition compared to the control | | |
|---|---|---|---|---|
| | | Gastric juice | Free acid | Total content |
| 250 | 16 | +17.3 | −23.0 | +11.8 |
| 500 | 8 | +15.2 | −19.1 | +16.5 |
| 1000 | 7 | −14.0 | −58.1$^x$ | −20.1 |

$^x$ = $p < 0.05$

Compound A in the doses employed did not change the gastric secretion except in very high doses, where a significant inhibition was revealed.

(6) ADJUVANT ARTHRITIS IN RATS METHOD

Adjuvant arthritis was produced by a single sc. injection of 0.25 mg of Mycobacterium tuberculosis suspended in 0.1 ml of mineral oil into the right hindpaw of male Long Evans rats (Newbould 1963). The initial paw volume was measured on the day of adjuvant injection. The swelling of the injected hindpaw (right) measured on the 10th day after the injection of adjuvant is considered as primary response and the increase in volume of the uninjected hindpaw (left) measured on day 15 constitutes the secondary response. The test compounds were dissolved in water (containing 0.2% of Tween-80) and administered p.o. once daily for 21 days. The first treatment was given on the day before the adjuvant injection, in a volume of 5 ml/kg body weight. Results are expresses as percent increase of paw volume compared to the initial volume.

TABLE 7

| Test-compound | Paw swelling, % | | % inhibition | |
|---|---|---|---|---|
| | Right | Left | Right | Left |
| Control | 117.1 ± 11.7 | 72.8 ± 16.6 | — | — |
| Compound A 100 mg/kg | 56.9$^{xx}$ ± 7.3 | 38.5 ± 8.8 | −51.4 | −47.1 |
| Phenylbutazone 30 mg/kg | 94.6 ± 14.3 | 36.7$^x$ ± 7.1 | −19.2 | −49.6 |

$^x$ = $p < 0.05$; $^{xx}$ = $p < 0.01$

Compound A in a dose of 100 mg/kg is more active than Phenylbutazone on the primary inflammation while on the secondary (immunological) inflammation the effect of Phenylbutazone and Compound A was equal in the employed doses.

(7) ANTIPYRETIC ACTIVITY IN RATS METHOD

The experiments were performed in groups of 10 Wistar rats of both sexes weighing 160–200 g. Fever was induced by 20% brewer's yeast suspended in 0.9% saline solution, applied subcutaneously in a volume of 2 ml/rat distributed at various sites of the back. After 18 hours the test compound or the vehicle was administered in a volume of 10 ml/kg p.o. During this period the rats were fasted but received drinking water ad libitum. The rectal temperature of the animals was measured with a Thermotest thermometer 2 days before injection of the fever inducer, then before the application of the test compound and after treatment in every 60th min. Animals with increase in body temperature less than 0.8° C. were excluded. The results were evaluated according to the statistical method of Duncan.

TABLE 8

| Test compound | Dose mg/kg | Antipyretic activity in rats Decrease in body temperature in °C. hours following treatment | | |
|---|---|---|---|---|
| | | 1 | 3 | 5 |
| Compound A | 100 | 1.5 | 2.0 | 1.7 |
| | 200 | 1.5 | 2.4 | 1.6 |
| Acetylsalicylic acid | 200 | 0.7 | 1.0 | 1.0 |
| Amidazophen | 200 | 2.7 | 2.3 | 1.7 |

Compound A shows significant antipyretic activity which surpasses that of acetylsalicylic acid.

(8) EFFECT OF CHEMILUMINESCENCE METHOD

Compound A was dissolved in dimethyl-sulfoxide (DMSO) in a concentration of $10^{-1}$ M, dilutions were made in the incubation medium employed.

Heparinized blood (10 IU/ml) was taken from healthy volunteers. The blood diluted with equal volume of dextran, the white blood cells were separated by sedimentation. The granulocytes were separated by Uromio gradient. The mononuclear cells were separated by centrifugation in Ficoll-Uromio gradient (specific gravity 1.078; 30 min., 2000 rpm). The cells were washed twice with Parker TC-199 medium and suspended in the same medium ($10^6$ cells/ml). The cell suspension was put in dark box for 15 min. Luminol was dissolved in concentrated $NH_4OH$ and diluted in the following solution:
50 ml Tris-Parker medium (containing 1.2 g Tris, pH=7.4)
150 ml Parker tissue culture medium
4 ml glucose 40% w/v in water The final concentration of Luminol was 32 $\mu M$. The Luminol solution (500 $\mu l$) was measured in plastic vials and put in dark (37° C.). The reaction was started by addition of the cells and stimulating agent (Phytohaemaglutinin-PHA 10 $\mu g/ml$).

The vials were continuously and gently shaken and the PHA stimulation was measured in every 2.5 min. for 15 min. in a Beckmann LS-100 spectrometer (coincidence switched off). The percentage of the counts measured was calculated in comparison with the solvent treated control cells. At least 5 concentrations of each compound were investigated in at least 3 parallels.

TABLE 9

| Chemiluminescence of PHA stimulated granulocytes | | |
|---|---|---|
| Test-compound | | $IC_{50}$ |
| Compound A | | $10^{-7}$ M |
| Phenylbutazone | | $10^{-4}$ M |
| Indomethacin | above | $10^{-4}$ M |
| Piroxicam | | $10^{-4}$ M |

Compound A inhibited the chemically induced appearance of free radicals; its activity surpasses that of the investigated anti-inflammatory agents by several order of magnitude. In mononuclear cells the $IC_{50}$ volume of Compound A as $3.10^5$ M, Piroxicam and Phenylbutazone were inactive in these cells. Compound A did not influence the chemiluminescence induced by $H_2O_2$ in cell free medium.

CONCLUSION

On the basis of the chemiluminescence measurements Compound A inhibits the formation of free oxygen radicals. These free radicals cause tissue damages, the inhibition of the formation of these radicals may give a therapeutic usefulness. Agents active in this respect may be employed as anti-inflammatory agents and may inhibit the process of ageing. As it is known, in the process of ageing the damage of structural elements caused by free oxygen radicals plays an important role.

The following reference compounds are used in the above tests:
Paracetamol=4-hydroxy-acetanilide;
Phenylbutazone=3,5-dioxo-1,2-diphenyl-4-(n-butyl)-pyrazolidine;
Indomethacine=1-(p-chloro-benzoyl)-5-methoxy-2-methyl-1H-indole-3-acetic acid;
Papaverine=1-[(3,4-dimethoxy-phenyl)-methyl)]-6,7-dimethoxy-isoquinoline;
Amidazophen=1-phenyl-2,3-dimethyl-4-dimethylamino-pyrazolone-5;
Piroxicam=4-hydroxy-2-methyl-N-2-pyridyl-2H-1,2-benzothiazine-3-carboxamide-1,1-dioxide.

The above tests are carried out by standard methods: reference is made to the following citations:
Litchfield, J. T., Wilcoxon, F.: J. Pharmacol. exp. Ther., 96, 99–113 (1949);
Newbould, B. B.: Brit. J. Pharmacol. 35, 487 (1969);
Shay, H., Kemarov, S. A., Fels, S. S., Meranze, D., Gruenstein, M., Siplet, H.: Gastroenterology 5, 45 (1945);
Stickney, J. C., Northup, D. W., Van Liere, E. J.: Arch. int. Pharmacodyn. 147, 113 (1964);
Winter, C. A., Risley, E. A., Nuss, G. W.: Proc. Soc. Exp. Biol. Med. 111, 544–547 (1962).

The pharmaceutical compositions of the present invention may be prepared by methods known per se by admixing 2,4-diamino-5-(3,4-dimethoxybenzyl)-pyrimidine or a pharmaceutically acceptable acid addition salt thereof with suitable inert solid or liquid pharmaceutical carriers.

The acid addition salts of 2,4-diamino-5-(3,4-dimethoxybenzyl)-pyrimidine may be salts formed with pharmaceutically acceptable inorganic or organic acids. Thus the following preferable salts may be mentioned: hydrochloride, hydrobromide, sulfate, phosphate, acetate, citrate, tartrate, maleate, fumarate, lactate etc. The 2,4-diamino-5-(3,4-dimethoxybenzyl)-pyrimidine or pharmaceutically acceptable acid addition salts thereof may be finished in forms suitable for oral, rectal or parenteral administration. The compositions suitable for oral administration may be e.g. tablets, pills, coated pills, dragées, enterosolvent tablets or dragées or capsules. The active ingredient content of the said compositions may be preferably between about 100 mg and about 500 mg.

The oral compositions may contain carriers and/or auxiliary agents generally used in pharmaceutical industry, e.g. lactose, starch, magnesium stearate, sodium citrate, calcium carbonate, dicalcium phosphate, starch derivatives (e.g. carboxymethyl starch), silicic acid or binding agents (e.g. polyvinyl pyrrolidone etc.) or sliding agents (e.g. magnesium stearate or talc etc.).

The compositions suitable for oral administration may also be finished in the form of aqueous suspension or elixir. The said compositions may comprise as diluent e.g. water, ethanol, propylene glycol or glycerol in addition to usual additives, e.g. colour-improving agents, dyestuffs, emulsifying or stabilizing agents (e.g. methyl-p-hydroxy benzoate etc.).

The tablets may be prepared according to a dry or wet granulating procedure. Dragées are obtained by preparing the dragée core and coating the same with a suitable coating layer by known methods. Capsules are prepared by filling a suitable mixture of the components into soft or hard gelatine capsules.

Suppositories suitable for rectal administration contain generally from about 0.1 g to about 0.5 g of the active ingredient. Suppositories may be prepared by uniformly distributing the active ingredient in the melt suppository base (e.g. cocoa butter, Witepsol H15 etc.), filling the melt into suitable forms, cooling the same and packing the suppositories into aluminum foil or tinfoil.

Injections suitable for parenteral use may be administered intravenously, intramuscularly, intraperitoneally or subcutaneously. The active ingredient content of the injectable solutions may vary preferably between about 0.05 g/ml and about 0.25 g/ml. Injectable solutions are advantageously filled into 1 ml or 2 ml ampoules; the active ingredient content of the said ampoules amounts preferably to about 0.025-0.25 g/ampoule. Injectable solutions suitable for parenteral administration contain as diluent preferably water, sesam oil, peanut oil, aqueous propylene glycol or any other pharmaceutically acceptable solvent. It is preferred to prepare aqueous solutions. Injectable solutions comprise 2,4-diamino-5-(3,4-dimethoxybenzyl)-pyrimidine preferably in the form of a water soluble salt thereof. Aqueous solutions may be buffered, if necessary, by methods known per se or can be made isotonic with the aid of a suitable amount of sodium chloride or glucose. the solutions thus obtained may be sterilized by known methods, if necessary.

The daily dosage of 2,4-diamino-5-(3,4-dimethoxybenzyl)-pyrimidine or an acid addition salt thereof may vary between wide ranges. Adult patients may receive for the relief of mild or medium-strong pains (e.g. head-ache, tooth-ache, lumbago, back-ache, neuralgia, myalgia, cold accompanied by fever, post-operation pains etc.) one or two tablets having an active ingredient content of 100-500 mg twice or three times a day.

In case of chronical rheumatic inflammations and degenerative rheumatism 8-10 tablets per day may be administered, particularly two tablets every 6th-8th hour.

The preferred daily dose for children is 3-4 times half a tablet or one tablet having an active ingredient content of 100-500 mg.

The daily dosage of 2,4-diamino-5-(3,4-dimethoxybenzyl)-pyrimidine amounts generally to about 50-8000 mg in various indications.

As analgesic and antipyretic agent the daily dose amounts to 50-4000 mg, administered in three or four portions a day. Children up to an age of 11 years may preferably receive a daily dose of 50-500 mg, while adults may preferably obtain 500-4000 mg.

In the treatment of rheumatic inflammations and rheumatism of various origin (degenerative or non-arthritic) the preferred dose may be about 1000-3000 mg for children and 3000-8000 mg for adults.

We wish to emphasize that the above ranges are but of an informative character and the actual dose is always determined by taking into consideration all circumstances of the given case and the prescriptions of the physician. Thus the actual dose may be lower or higher than the above range as well.

2,4-Diamino-5-(3,4-dimethoxybenzyl)-pyrimidine and pharmaceutically acceptable acid addition salts thereof may be prepared by methods disclosed in prior art. thus numerous methods are disclosed for the preparation of the said compound. Reference is made to the following citations:

J. Am. Chem. Soc. 73, 3758-3762 (1951); J. Med. Chem. 14, (5) 462-463 (1971); J. Org. Chem. 28, 1983-1988 (1963); Acta Chim. Acad. Sci. Hung. 87, (2) 177-182 (1975); U.S. Pat. Nos. 2,624,731 and 3,049,544; UK patent No. 957,797; Dutch patent specifications Nos. 65.14178 and 66.15287; Hungarian patent specifications Nos. 149,799,150,699, 153,325 and 162,316.

Thus 2,4-diamino-5-(3,4-dimethoxybenzyl)-pyrimidine may be particularly preferably prepared by reacting 3,4-dimethoxy-benzaldehyde with β-methoxy-propionitrile, reacting the α-(3,4-dimethoxy-benzal)-β-methoxy-propionitrile thus obtained first with a mono-(lower alkyl)-ether of ethylene glycol or diethylene glycol and thereafter with guanidine or an acid addition salt thereof and, if desired, converting the 2,4-diamino-5-(3,4-dimethoxybenzyl)-pyrimidine thus obtained into a pharmaceutically acceptable acid addition salt thereof.

According to a further aspect of the present invention there is provided a process for the preparation of pharmaceutical compositions—particularly those having analgesic and/or anti-inflammatory effect—which comprises admixing 2,4-diamino-5-(3,4-dimethoxybenzyl)-pyrimidine or a pharmaceutically acceptable acid addition salt thereof with suitable inert solid or liquid carriers.

The above process is carried out by methods of pharmaceutical industry known per se.

According to a still further aspect of the present invention there is provided the use of 2,4-diamino-5-(3,4-dimethoxybenzyl)-pyrimidine or a pharmaceutically acceptable acid addition salt thereof for the preparation of pharmaceutical compositions, particularly those having analgesic and/or anti-inflammatory effect.

The advantage of the pharmaceutical compositions of the present invention comprising as active ingredient 2,4-diamino-5-(3,4-dimethoxybenzyl)-pyrimidine or a pharmaceutically acceptable acid addition salt thereof resides particularly in the fact that the analgesic and anti-inflammatory effect thereof surpasses that of drugs known in this field of therapy while the compositions of the present invention are devoid of the gastric mucosa damaging side-effects being characteristic of the known anti-inflammatory and analgesic agents. Thus the compositions of the present invention exhibit the desired analgesic and anti-inflammatory effect without causing undesired ulcerogenic side-effects.

Further details of the present invention are to be found in the following Examples without limiting the scope of protection to the said Examples.

EXAMPLES

I.

Examples relating to the preparation of the active ingredient.

EXAMPLE 1

A mixture of 200 g (1.20 mole) of 3,4-dimethoxy-benzaldehyde, 150 g (1.75 mole) of β-methoxy-propinitrile, 260 ml of methanol and 10 g of a 55% methanolic potassium hydroxide solution is stirred at 60°–62° C. for 8 hours, whereupon the reaction mixture is cooled to 30° C., and 170 g of a 55% methanolic potassium hydroxide solution are added dropwise. The reaction mixture is stirred for 5 hours and diluted with 1000 ml of water. The precipitated crystalline product is filtered, washed with methanol and water. Thus 280 g of α-(3,4-dimethoxy-benzal)-β-methoxy-propionitrile are obtained, yield 85%, mp.: 82°–83° C.

A mixture of 175 g (0.75 mole) of α-(3,4-dimethoxy-benzal)-β-methoxy-propionitrile, 240 ml of diethylene glycol monomethyl ether and 11 g of sodium methylate is stirred at 75°–77° C. for 3 hours, whereupon the mixture is cooled and 320 ml of isobutanol, 170 g of guanidine hydrochloride and 100 g of sodium methylate are added. The reaction mixture is warmed slowly to 90°–92° C. and stirred at this temperature for 7 hours. The reaction mixture is cooled to room temperature, the precipitated crystals are filtered and washed with water and methanol. After recrystallization from a 1:1 mixture of water and methanol 152 g of 2,4-diamino-5-(3,4-dimethoxy-benzyl)-pyrimidine are obtained, yield 78%, mp.: 231°–232° C.

EXAMPLE 2

2,4-Diamino-5-(3,4-dimethoxy-benzyl)-pyrimidine is reacted with a stoichiometrical amount of acetic acid, citric acid and tartaric acid, respectively, in a manner known per se. The melting points of the salts thus obtained are summarized in Table 10.

TABLE 10

| Salt | Mp., °C. |
| --- | --- |
| Acetate | 232–234 |
| Citrate | 98–102 |
| Tartarate | 138–140 |

II.

Examples relating to the preparation of pharmaceutical compositions.

EXAMPLE 3

Tablets having the following composition are prepared by methods of pharmaceutical industry known per se:

| Component | Amount, g/tablet |
| --- | --- |
| 2,4-Diamino-5-(3,4-dimethoxy-benzyl)-pyrimidine | 0.250 |
| Lactose | 0.110 |
| Potato starch | 0.055 |
| Sodium amylopectine glycolate | 0.010 |
| Gelatine | 0.008 |
| Magnesium stearate | 0.001 |
| Total weight | 0.434 g |

EXAMPLE 4

Tablets having the following composition are prepared by methods of pharmaceutical industry known per se:

| Component | Amount, g/tablet |
| --- | --- |
| 2,4-Diamino-5-(3,4-dimethoxy-benzyl)-pyrimidine | 0.500 |
| Lactose | 0.150 |
| Potato starch | 0.080 |
| Sodium amylopectine glycolate | 0.020 |
| Gelatine | 0.016 |
| Magnesium stearate | 0.002 |
| Total weight | 0.768 g |

EXAMPLE 5

Suppositories having the following composition are prepared by methods of pharmaceutical industry known per se:

| Component | Amount, g/suppository |
| --- | --- |
| 2,4-Diamino-5-(3,4-dimethoxy-benzyl)-pyrimidine | 0.250 |
| Witepsol H 15 | 1.340 |

EXAMPLE 6

Suppositories having the following composition are prepared by methods of pharmaceutical industry known per se:

| Component | Amount, g/suppository |
| --- | --- |
| 2,4-Diamino-5-(3,4-dimethoxy-benzyl)-pyrimidine | 0.500 |
| Witepsol H 15 | 1.500 |

EXAMPLE 7

Injectable solutions are prepared by methods of pharmaceutical industry known per se:

| Component | Amount |
| --- | --- |
| 2,4-Diamino-5-(3,4-dimethoxy-benzyl)-pyrimidine | 0.2500 g |
| Ascorbic acid | 0.187 g |
| Distilled water ad | 2.0 ml |

EXAMPLE 8

An injectable solution having the following composition is prepared by methods of pharmaceutical industry known per se:

| Component | Amount |
| --- | --- |
| 2,4-Diamino-5-(3,4-dimethoxy-benzyl) pyrimidine | 0.500 |
| Ascorbic acid | 0.374 g |
| Distilled water ad | 5.0 ml |

EXAMPLE 9

A suspension having the following composition is prepared by methods of pharmaceutical industry known per se:

| Component | Amount |
| --- | --- |
| 2,4-Diamino-5-(3,4-dimethoxy-benzyl)-pyrimidine | 5.0 g |
| Methyl-p-hydroxy-benzoate | 0.1 g |
| Spiritus anisatus | 0.25 g |
| Keltrol (xanthane gum) | 61.0 g |

| Component | Amount |
| --- | --- |
| Distilled water ad | 100.0 ml |

What we claim is:

1. A method of treating an individual in need of an analgesic or anti-inflammatory agent comprising administering to the individual a pharmaceutical composition containing a pharmaceutically effective amount of 2,4-diamino-5-(3,4-dimethoxy-benzyl)-pyrimidine or a pharmaceutically acceptable acid addition salt thereof.

2. The method of claim 1, wherein said composition contains said 2,4-diamino-5-(3,4-dimethoxy-benzyl)-pyrimidine or an acid addition salt thereof in admixture with an inert pharmaceutically acceptable solid or liquid carrier.

3. The method of claim 2, wherein said composition is administered orally, rectally or parenterally.

4. The method of claim 3, wherein said composition is in the form of a tablet, capsule, pill, coated pill, dragée, solution, suspension, suppository or injection.

5. The method of claim 4, wherein said composition is in the form of a tablet, dragée or capsule having an active ingredient content of 100–500 mg.

6. The method of claim 4, wherein said composition is in the form of a suppository having an active ingredient content of 0.1–0.5 g.

7. The method of claim 4 wherein said composition is in the form of an injection having an active ingredient content of 0.05–0.25 g/ml.

* * * * *